(12) United States Patent
Cooper et al.

(10) Patent No.: US 6,361,800 B1
(45) Date of Patent: Mar. 26, 2002

(54) MULTI-VITAMIN AND MINERAL SUPPLEMENT

(75) Inventors: Kenneth H. Cooper; Ishwarlal Jialal; Scott Montgomery Grundy, all of Dallas, TX (US); Walter Churchill Willett, Cambridge; Jacob Selhub, Brookline, both of MA (US)

(73) Assignee: Cooper Concepts, Inc., Dallas, TX (US)

( * ) Notice: Subject to any disclaimer, the term of this patent is extended or adjusted under 35 U.S.C. 154(b) by 0 days.

(21) Appl. No.: 09/548,914

(22) Filed: Apr. 13, 2000

(51) Int. Cl.[7] .................. A61K 33/34; A61K 33/32; A61K 33/36; A61K 33/14; A61K 33/04

(52) U.S. Cl. .................. 424/630; 424/641; 424/655; 424/669; 424/677; 424/702

(58) Field of Search .................. 424/630, 641, 424/655, 669, 677, 702

(56) References Cited

PUBLICATIONS

Francesco Nappo, MD, Ph.D. et al, "Impairment of Endothelial Functions by Acute Hyperhomocysteinemia and Reversal by Antioxidant Vitamins" American Medical Association, JAMA, vol. 281, No. 22, pp. 2113–2118. (Jun. 9, 1999).

L. Riddell, Alexandra Chisholm Sheila Williams, and Jim Mann, "Dietary Strategies for Lowering Homocysteine Concentrations [1–3]", Am J. Clinical Nutrition 2000, 71:pp. 1448–1458; (Nov. 11, 1999).

George N. Welch, MD., Joseph Loscalzo, MD., Ph.D, "Homocysteine and Atherotherombosis" The New England Journal of Medicine, pp. 1042–1050, (Apr. 9, 1998).

Jayne V. Woodside, et al., Effect of B–group Vitamins and Antioxidant Vitamins on Hyperhomocysteinemia: A Double–blind, Randomized, Factorial—design, controlled trial [1–3], Am. Journal of Clinical Nutrition; 67, pp. 858–866, (1998).

Sridevi Devaraj and Ishwarlal Jialal, "Alpha–Tocopherol Decreases Interleukin–1β Release From Activated Human Monocytes by Inhibition of 5–Lipoxygenase", Center for Human Nutrition (S.D., I.I.) and Departments of Pathology (S.D., I.J.) and Internal Medicine (I.J.) University of Texas, Southwestern Medical Center, Dallas, TX. pp. 1125–1133, (Oct. 28, 1998).

Ishwarlal Jialal, Cindy J. Fuller and Beverley A. Huet, "The Effect of Alpha–Tocopherol Supplementation of LDL Oxidation: A Dose–Response Study", American Heart Association, Inc., Center for Human Nutrition, UT Southwestern Medical Center, pp. 190–198, (1995).

Olli P. Heinonen, et al., Prostate Cancer and Supplementation with Alpha–Tocopherol and β–Carotene: Incidence and Mortality in a Controlled Trial; Journal of the National Cancer Institute, vol. 90., No. 6, pp. 440–446, (Mar. 18, 1998).

Paul F. Jacques, et al., "Long–Term Vitamin C Supplement Use and Prevalence of Early Age–Related Lens Opacities [1–4]", American Journal of Clinical Nutrition, 66:pp. 911–916, (1997).

Giuseppe Paolisso, et al, "Pharmacologic Doses of Vitamin E Improve Insulin Action in Healthy Subjects and Non–Insulin–Dependent Diabetic Patients [1,2]"; American Journal of Clinical Nutrition; 57:pp. 650–656, (1993).

Gary D. Plotnick, MD, Mary C. Corretti, And Robert A. Vogel,MD, "Effect of Antioxidant Vitamins on the Transient Impairment of Endothelium–Dependent Brachial Artery Vasoactivity Following a Single High–Fat Meal", JAMA, vol. 278, No. 20 pp. 1682–1688, (Nov. 26, 1997).

Marco N. Diaz et al, "Antioxidants and Atherosclerotic Heart Disease", The New England Journal of Medicine, pp. 408–416, (Aug. 7, 1997).

Timothy E. McAlindon, et al., "Do Antioxidant Micronutrients Protect Against The Development and Progression of Knee Osteoarthritis", Arthritis & rheumatisum vol. 39, No. 4, pp. 648–656, (Apr. 1996).

Bernadette Eberlein–Konig, MD, Marianne Placzek, MD, and Bernhard Przybilla, MD, "Protective Effect Against Sunburn of Combined Systemic Ascorbic Acid (Vitamin C) and d–Alpha–Tocopherol (vitamin E)", J. Am Acad Dermatol, 38: pp. 45–48, (1998).

Johanna M. Seddon, et al., "Dietary Carotenoids, Vitamins A, C, and E, and Advanced Age–Related Macular Degeneration", JAMA,vol. 272, No. 18, pp. 1413–1420, (Nov. 9, 1994).

Nigel G. Stephens, et al., "Randomised Controlled Trial of Vitamin E in Patients with Coronary Disease: Cambridge Heart Antioxidant Study (CHAOS)",The Lancet, vol. 347, pp. 781–786, (Mar. 23, 1996).

Meir J. Stamper, MD., et al., "Vitamin E Consumption and the risk or coronary Disease in Women", the New England Journal of Medicine, vol. 328, No. 20, pp., 1444–1449, (May 20, 1993).

Eric B. Rimm, Sc.D., et al, "Vitamin E Consumption and the risk of Coronary Heart Disease in Men", The New England Jour5nal of Medicine, vol. 328, No. 20, pp. 1450–1456, (May 20, 1993).

Andreas Hartmann, et al., "Vitamin E. Prevents Exercise–Induced DNA Damage", Mutation Research 346, pp. 195–202, (1995).

(List continued on next page.)

*Primary Examiner*—Dwayne C. Jones
(74) *Attorney, Agent, or Firm*—Arter & Hadden LLP

(57) ABSTRACT

This invention is directed to a multi-vitamin and mineral supplement which supplies the right amount of the right micronutrients at the right time to assure adequate intake of micronutrients needed for disease prevention and protection against nutritional losses and deficiencies due to lifestyle factors and common inadequate dietary patterns. The multi-vitamin and mineral supplement is comprised of vitamin A, vitamin C, vitamin D, vitamin E, vitamin K, vitamin B1, vitamin B2, niacinamide, vitamin B6, vitamin B12, biotin, pantothenic acid, iron, phosphorus, iodine, magnesium, zinc, selenium, copper, chromium, potassium, choline, lycopene, and co-enzyme Q-10.

29 Claims, No Drawings

OTHER PUBLICATIONS

Ranjit Kumar Chandra, "Graying of the Immune System: Can Nutrient Supplements Improve Immunity in the Elderly", JAMA, vol. 277, No. 17,.pp. 1398–1399, (May 7, 1997).

Meir J. Stampfer, MD, et al., "A Prospective Study of Plasma Homocyst(e)ine and Risk of Myocardial Infarction in US Physicians", JAMA vol., 268, No. 7, pp. 877–881, (Aug. 19, 1992).

Jacob Selhub, Ph.D., et al., "Association Between Plasma Homocysteine Concentrations and Extracranial Carotid–Artery Stenosis" The New England Journal of Medicine, pp. 286, (Feb. 2, 1995).

Hans J. Naurath, et al., "Effects of Vitamin B12, Folate, and Vitamin B6 Supplements in Elderly people with Normal Serum Vitamin Concentrations", The Lancet, vol., 346, pp. 85–89, (Jul. 8, 1995).

Egil Arnesen, et al., Serum total Homocysteine and Coronary Heart Disease International Journal of Epidemiology, vol. 24, No. 4, pp. 704–709, (1995).

Carol J. Boushey, PhD, et al., "A Quantitative Assessment of Plasma Homocysteine as a Risk Factor for Vascular Disease", JAMA, vol. 274, No. 13, pp. 1049–1057, (Oct. 4, 1995).

Ottar Nygard, MD, et al., "Total Plasma Homocysteine and Cardiovascular Risk Profile: The Hordaland Homocysteine Study", JAMA, vol. 274, No. 19, pp. 1526–1533, (Nov. 15, 1995).

Nicholas J. Wald, DSc, et al., "Homocysteine and Ischemic Heart Disease", Arch Intern Med., vol. 158, pp. 862–867, (Apr. 27, 1998).

Manuel r. Malinow, et al., Reduction of Plama Homocyst (e) ine Levels By breakfast Cereal Fortified with Folic Acid in Patients With Coronary Heart Disease, The New England Journal of Medicine, vol. 338, No. 15, pp. 1009–1015, (Apr. 9, 1998).

Simin Nikbin Meydani, et al., "Vitamin E Supplementation and In Vivo Immune Response in Healthy Elderly Subjects", JAMA, vol. 277, No. 17, pp. 1380–1386, (May 7, 1997).

Ian M. Graham, et al., "Plasma Homocysteine as a Risk Factor for Vascular Disease: The European Concerted Action Project", JAMA, vol. 277, No. 22, pp. 1775–1781, (Jun. 11, 1997).

Eric B. Rimm, et al., "Folate and Vitamin $B_6$ From Diet and Supplements in Relation to Risk of Coronary Heart Disease Among Women", JAMA, vol. 279, No. 5, pp. 359–364, (Feb. 4, 1998).

Dienneke ZB van Asselt, et al., Role fo Colbalamin Intake and Atrophic Gastritis in Mild Cobalamin Deficiency in Older Dutch Subjects [1–3], Am. Journal Clinical Nutrition;68: pp. 328–334, (1998).

Katherine L. Tucker, et al., "Folic Acid Fortification of the Food Supply", JAMA, vol. 276, No. 23, pp. 1879–1714, (Dec. 18, 1996).

Tomoko Shimakawa, et al., "Vitamin Intake: A Possible Determinant of Plasma Homocyst (e) ine Among Middle-–Aged Adults", AEP, vol. 7, No. 4., pp. 285–293, (May 1997).

Gilbert S. Omenn, et al., "Preventing Coronary Heart Disease B Vitamins and Homocysteine", American Heart Association, Inc., pp. 421–424, (1998).

Ottar Nygard, et al., "Plasma Homocysteine Levels and Mortality in Patients with Coronary Artery Disease", The New England Journal of Medicine, vol. 337, No. 4, pp. 230–236, (Jul. 24, 1997).

Edward Giovannucci, et al., "Multivitamin Use, Folate, and Colon Cancer in Women in the Nurses' Health Study" Annals of Internal Medicine, vol. 129, No. 7, pp. 517–524, (Oct. 1, 1998).

Anja Bronstrup, et al., Effects of Folic Acid and combinations of Folic Acid and Vitamin B–12 on Plasma Homocysteine Concentrations in Healthy, Young Women [1,2], Am. Journal Clinical Nutrition, vol. 68, pp. 1104–1110, (1998).

Larry C. Clark, et al., "Effects of Selenium Supplementation for Cancer Prevention in Patients With Carcinoma of the Skin: A Randomized Controlled Trial", JAMA, vol. 276, No. 24, pp. 1957–1963, (Dec. 25, 1996).

Melissa K. Thomas, et al., "Hypovitaminosis D in Medical inpatients", The New England Journal of Medicine, vol. 338, No. 12, pp. 777–783, (Mar. 19, 1998).

Mary Sano, et al., "A Controlled Trial of Selegiline, Alpha–Tocopherol, or Both as Treatment for Alzheimer's Disease", The New England Journal of Medicine, vol. 336, No. 17, pp. 1219–1222, (Apr. 24, 1997).

C. Douillet, et al., "Effect of Selenium and Vitamin E. Supplements on Tissue Lipids, peroxides, and Fatty Acid Distribution in Experimental Diabetes", Lipids, vol. 33, No. 4, pp. 393–399, (1998).

Killian Robinson, et al., "Low Circulating Folate and Vitamin $B_6$ Concentrations risk Factors for Stroke, peripheral Vascular Disease, and Coronary Artery Disease", American Heart Association, Inc., pp. 437–443, (1998).

L.C. Clark' et al., "decreased Incidence of Prostate Cancer with Selenium Supplementation: Results of a Double–Blind Cancer Prevention Trial", British Journal of Urology, vol. 81, pp. 730–734, (Jan. 12, 1998).

R. Aejmelaeus, et al., "Ubiquinol–10 and Total Peroxyl Radical Trapping Capacity of LDL Lipoproteins During Aging: The Effects of Q–10 Supplementation", Molec. Aspects Med., vol. 18, pp. s113–s120, (1997).

Knud Lockwood, et al., "Partial and Complete Regression of Breast Cancer in Patients in Relation to Dosage of Coenzynme $Q_{10}$", Biochemical and Biophysical Research Communications, vol. 199, No. 3, pp. 1504–1508, (Mar. 30, 1994).

Francene M. Steinberg, et al., "Antioxidant Vitamin Supplementation and Lipid Peroxidation in Smokers[1–3]", Am J. Clin. Nutr., vol. 68, pp. 319–327, (1998).

Thomas Heitzer, et al., "Antioxidant Vitamin C Improves Endothelial Dysfunction in Chronic Smokers", Brief Rapid Communications, pp. 6–9, (1996).

Sanjiv Agarwal, et al., "Tomato Lycopene and Low Density lipoprotein Oxidation: A Human Dietary Intervention Study", Lipids, vol. 33, No. 10, pp. 981–983, (1998).

Joel A. Simon, et al., "Serum Ascorbic Acid and Other Correlates of Gallbladder Disease Among US Adults", American Journal of public Health, vol. 88, No. 8, pp. 1208–1212, (Aug. 1998).

Aaron R. Folsom, et al., Prospective Study of Coronary Heart Disease Incidence in relation to Fasting Total homocysteine, related Genetic Polymorphisms, and B Vitamins: The Atherosclerosis Risk in Communities (ARIC) Study, Clinical Investigation and Reports, vol. 98, pp. 204–210, (1998).

Joel A. Simon, et al., "Ascorbic Acid Supplement Use and the Prevalence of gallbladder Disease", J. Clin Epidemiol, vol. 51, No. 3, pp. 257–265, (1998).

Brigitte M. Winklhofer–Roob, et al., "Impaired resistance to oxidation of Low Density Lipoprotein in Cystic Fibrosis: Improvement During Vitamin E Supplementation", Free Radical Biology & Medicine, vol. 19, No. 6, pp. 725–733, (1995).

L. John Hoffer, "Nutritional Supplements and Health", Annals RCPSE, vol. 29, No. 1, pp. 11–16, (Feb. 1996).

"Environmental Nutrition" vol. 17, No. 10., pp. 3–4, (Oct. 1994).

Pauline Mendola, et al., "Dietary Correlates of Fat Intake", Nutrition and Cancer, vol. 23, No. 2, pp. 161–169, (1995).

Ralph L. Sacco, et al., "Homocysteine as A Risk Factor for Ischemic Stroke: An Epidemiological Story", Neuroepidemiology, vol. 17, pp. 167–173, (1998).

MULTI-VITAMIN AND MINERAL SUPPLEMENT

BACKGROUND OF THE INVENTION

This invention relates to multi-vitamin and mineral supplements. In particular, this invention relates to multi-vitamin and mineral supplements for improving health by insuring adequate intake of micronutrients needed for disease prevention and protection against nutritional losses and deficiencies due to such factors as lifestyle patterns and common inadequate dietary patterns.

Vitamin and mineral preparations are commonly administered to treat specific medical conditions or as general nutritional supplements. Micronutrients are elements or compounds which are present in foods in small or trace amounts and includes vitamins, minerals, or other elements, and compounds found in foods for which a Recommended Daily Allowance (RDA) has not yet been determined. The macronutrients consist of carbohydrates, fats, and proteins which supply nutrients and calories. Some elements such as calcium, sodium, potassium, chloride, and phosphorus are consumed in relatively large amounts, while many such as iron, iodine, and zinc are consumed in small amounts. vitamins such as B12 and folic acid and the minerals cooper, selenium, and chromium are consumed in very small or trace amounts. In as much as the human body does not synthesize many compounds which are essential to the human body, these specific vitamins and minerals can be obtained from only two sources: food and supplements. The primary source of all nutrients is food. However, the majority of people do not meet the RDA of the foods containing these essential compounds and elements. Thus vitamin and mineral supplementation has become a recognized method of meeting accepted medical and health standards.

An international panel of diet and cancer experts announced in London on Sep. 30, 1997, that as many as 30 to 40 percent of all cancer cases worldwide—3 to 4 million a year—could be avoided if people ate a healthy diet and got enough exercise. *USA Today*, Oct. 1, 1997. However, for some nutrients, the amounts proposed as being healthy apparently cannot be provided by a reasonable quantity and variety of natural foods. Thus nutrient supplements may be important for health promotion and prevention of chronic diseases. *Journal of the American Medical Association*, May 7, 1997.

Recent studies have illustrated the important physiological roles played by vitamins and minerals and established a correlation between deficiencies or excesses of these nutrients and the etiologies of certain disease states in humans. Homocysteine is a homolog of cysteine and is produced by the demetbylation of methionine, and is an intermediate in the biosynthesis of cysteine from methionine via cystathionine. Homocysteine is being referred to as the "cholesterol of the $21^{st}$ century." Homocysteine is not inherently bad, as it is a necessary by-product in the break down of the essential amino acid methionine, which is found primarily in red meat and diary products. However, as with cholesterol, homocysteine may get out of balance as a result of genetics or poor diet. The main concern is having too much homocysteine.

As stated in the *Journal of the American Medical Association*, "A high level of homocysteine confers a risk of vascular disease similar to that of cigarette smoking, elevated cholesterol, and other blood lipids. Also, it increases the risk associated with smoking and high blood pressure." *Journal of the American Medical Association*, Jun. 11, 1997. Elevated blood levels of homocysteine increase the risk of atherosclerosis, a clogging of the arteries that is the main factor in the majority of heart attacks and strokes. Elevated homocysteine levels are found in 25% of heart attack patients, 40% of stroke patients, and may also be associated with Alzheimer's disease.

It has recently been discovered that folic acid, when combined with vitamins B6 and B12, has the potential of dramatically lower the homocysteine levels, thereby protecting against high homocysteine-related diseases. *Journal of the American Medical Association*, Oct. 4, 1995.

Coronary artery disease is one of the major causes of heart attacks and occurs when there is atherosclerosis in the vital coronary arteries, which supply the nutrient rich blood to the interior of the heart muscle. High levels of LDL cholesterol have been linked to the development of atherosclerosis in the coronary arteries. However, free radicals have received more attention as the culprit of the disease. It appears that clogging occurs after the LDL cholesterol is oxidized within the wall of the blood vessel by exposure to free radicals. The white blood cells attempt to remove the damaged LDL cholesterol by engulfing them. Unfortunately, after ingesting the LDL cholesterol, the cells cannot rid themselves of the cholesterol portion and swell up, thus the process of atherosclerosis (thickening of the artery wall and narrowing of the coronary arteries) begins. Therefore, it is not the LDL cholesterol that blocks the artery, but the oxidized LDL that has been engulfed by the white blood cells that actually causes the damage.

Free radicals may be activated by factors such as cigarette smoke, pollution, excessive exercise, and other stressors. The LDL cholesterol can fight these free radicals with antioxidants such as vitamins C and E, but before long the LDL's antioxidants are depleted and the LDL is left defenseless. It has been discovered that 1000 mg of vitamin C coupled with 1000 I.U. of vitamin E (d-alpha tocopherol) taken in conjunction with a 900-calorie meal containing 50 grams of fat blocked the detrimental effects of a fatty meal on blood circulation. *Journal of the American Medical Association*, Nov. 26, 1997. In addition, it has been discovered that 100 I.U. of vitamin E supplements taken for two years or longer reduced deaths of coronary artery disease by 40% in 87,245 nurses and by 37% in 39,910 male health professionals. *New England Journal of Medicine*, May 20, 1993.

There exists a need for a nutritional supplement which supplies the right amount of the right micronutrients at the right time to assure adequate intake of micronutrients needed for disease prevention and protection against nutritional losses and deficiencies due to lifestyle factors and common inadequate dietary patterns.

SUMMARY OF THE INVENTION

In accordance with the present invention, there is provided a multi-vitamin and mineral supplement which supplies the right amount of the right micronutrients at the right time to assure adequate intake of micronutrients needed for disease prevention and protection against nutritional losses and deficiencies due to lifestyle factors and common inadequate dietary patterns.

Further, in accordance with the present invention, there is provided a new and improved multi-vitamin and mineral supplement which can be used for providing the necessary nutrients to allow the users of such supplement to maintain their present health and positively influence their future health.

Still further in accordance with the present invention, there is provided a multi-vitamin and mineral supplement wherein the supplement is comprised of about 5000 I.U. of vitamin A; about 1000 mg of vitamin C; about 400 I.U. of vitamin D; about 400 I.U. of vitamin E; about 25 mg of vitamin K; about 3 mg of vitamin B1; about 10 mg of vitamin B2; about 20 mg of niacinamide; about 50 mg of vitamin B6; about 800 mcg of folic acid; about 400 mcg of vitamin B12; about 300 mcg of biotin; about 10 mg of pantothenic acid; about 18 mg of iron dosed in the form of a pharmaceutically acceptable iron compound; dosed in the form of a pharmaceutically acceptable phosphorus compound; about 150 mcg of iodine dosed in the form of a pharmaceutically acceptable iodine compound; about 400 mg of magnesium dosed in the form of a pharmaceutically acceptable magnesium compound; about 15 mg of zinc dosed in the form of a pharmaceutically acceptable zinc compound; about 100 mcg of selenium; about 2 mg of copper dosed in the form of a pharmaceutically acceptable copper compound; about 65 mcg of chromium dosed in the form of a pharmaceutically acceptable chromium compound; about 400 mg of potassium dosed in the form of a pharmaceutically acceptable potassium compound; about 500 mg of choline dosed in the form of a pharmaceutically acceptable choline compound; about 5 mg of lycopene; and about 100 mg co-enzyme Q-10 dosed in the form of a pharmaceutically acceptable co-enzyme Q-10 compound.

An advantage of the present invention is that the multi-vitamin and mineral supplement supplies the right amount of the right micronutrients at the right time to assure adequate intake of micronutrients needed for disease prevention and protection against nutritional losses and deficiencies due to lifestyle factors and common inadequate dietary patterns.

Another advantage of the present invention is that the multi-vitamin and mineral supplement provides the necessary nutrients to allow the users of such supplement to maintain their present health and positively influence their future health.

Another advantage of the present invention is that the multi-vitamin and mineral supplement decreases plasma homocysteine levels, reduces the susceptibility of LDL cholesterol to oxidation, and lowers plasma glucose levels.

These and other advantages and benefits of the invention will be apparent to those skilled in the art upon reading and understanding of the following detailed description.

DETAILED DESCRIPTION OF THE PREFERRED EMBODIMENT

This invention is directed to a multi-vitamin and mineral supplement comprised of about 5000 I.U. of vitamin A; about 1000 mg of vitamin C; about 400 I.U. of vitamin D; about 400 I.U. of vitamin E; about 25 mcg of vitamin K; about 3 mg of vitamin B1; about 10 mg of vitamin B2; about 20 mg of niacinamide; about 50 mg of vitamin B6; about 800 mcg of folic acid; about 400 mcg of vitamin B12; about 300 mcg of biotin; about 10 mg of pantothenic acid; about 18 mg of iron dosed in the form of a pharmaceutically acceptable iron compound; about 150 mcg of iodine dosed in the form of a pharmaceutically acceptable iodine compound; about 400 mg of magnesium dosed in the form of a pharmaceutically acceptable magnesium compound; about 15 mg of zinc dosed in the form of a pharmaceutically acceptable zinc compound; about 500 mcg of selenium; about 2 mg of copper dosed in the form of a pharmaceutically acceptable copper compound; about 65 mcg of chromium dosed in the form of a pharmaceutically acceptable chromium compound ; about 400 mg of potassium dosed in the form of a pharmaceutically acceptable potassium compound; about 500 mg of choline dosed in the form of a pharmaceutically acceptable choline compound; about 5 mg of lycopene; and about 100 mg co-enzyme Q-10 dosed in the form of a pharmaceutically acceptable co-enzyme Q-10 compound.

All amounts specified in the application are based on milligrams unless otherwise indicated. The term "I.U." represents International Units.

The multi-vitamin and mineral supplement is comprised of vitamin A. Vitamin A prevents night blindness and other eye disorders, keeps skin moist and elastic, maintains healthy hair, skin, and gums, reduces the risk of breast cancer, helps alleviate mastodynia, reduces the risk of lung cancer, maintains cell structure and integrity, works as antioxidant to prevent cell aging, helps prevent infection, and negates skin wrinkling and the effects of sun damage. vitamin A is a fat soluble vitamin. The term vitamin A is used to include retinol and other chemically similar compounds referred to as retanoids. Beta-carotene and other carotenoids are provitamins and are only turned into retinol as the body requires. Preferably, the mixed carotenoids are lutein and zeaxanthine. Lutein and zeaxanthine have been found to decrease the risk and even reverse the development of macular degeneration, the leading cause of blindness in those over the age of 65.

Preferably, in the multi-vitamin and mineral supplement, vitamin A is provided in the form of beta-carotene and other mixed carotenoids. Preferably, the multi-vitamin is comprised of about 5000 I.U of vitamin A and about 14 mcg of lutein and zeaxanthine. More preferably, the multi-vitamin and mineral supplement is comprised of about 5000 I.U. of vitamin A in the form of natural mixed beta-carotene and about 14 mcg of lutein and zeaxanthine.

Vitamin C, also known as ascorbic acid, is necessary for the synthesis of collagen and is used as an antioxidant. Vitamin C fights infection, reduces inflammation, heals wounds, reduces the risk of heart disease, lowers cholesterol, reduces the risk of lung, stomach, and esophageal cancers, reduces cervical epithelial abnormalities, inhibits N-nitrosamine, and reduces the severity of colds. Preferably, the multi-vitamin and mineral supplement is comprised of about 1000 mg of vitamin C.

Vitamin D is also an essential vitamin that is included in the multi-vitamin and mineral supplement of the present invention. Vitamin D assists in the mineralization and calcification of bone, prevents rickets in children, prevents osteomalacia in adults, preserves bone and tooth growth, and lowers blood pressure. Vitamin D is fat soluble. Preferably, the multi-vitamin and mineral supplement is comprised of about 400 I.U. of vitamin D.

Vitamin E is needed for the maintenance of cell membranes and for neurological health. Vitamin E relieves hot flashes, relieves mastodynia, helps in fighting fibrocystic breast disease, reduces mammary tumors, reduces the risk of lung cancer, and reduces the risk of heart disease. Vitamin E is the generic term for a group of related substances which include alpha-tocopherol, beta-tocopherol, gamma-tocopherol, and delta-tocopherol. In addition, each of these four compounds have a "d" form, which is the natural form, and a "dl" form which is the synthetic form. Preferably, in the multi-vitamin and mineral supplement, vitamin E is provided in the form of d-alpha tocopherol succinate. Preferably, the multi-vitamin and mineral supplement is comprised of about 400 I.U. of vitamin E. More preferably, the multi-vitamin and mineral supplement is comprised of about 400 I.U. of vitamin E in the form of d-alpha tocopherol succinate.

The multi-vitamin and mineral supplement includes vitamin K. Vitamin K is an active blood clotting agent and assists in bone formation. Preferably, the multi-vitamin and mineral supplement is comprised of about 25 mcg of vitamin K.

The multi-vitamin and mineral supplement is comprised of most of the B complex of vitamins. The B vitamins are water-soluble. The B vitamins included in the multi-vitamin and mineral supplement are thiamin (vitamin B1), riboflavin (vitamin B2), niacin (vitamin B3), pantothenic acid (vitamin B5), pyridoxine (vitamin B6), biotin, folic acid, the cobalamins (vitamin B12), and choline.

Vitamin B1 or thiamin helps keep collagen-rich connective and mucous membranes healthy, helps to maintain smooth muscles, helps in the formation of blood cells, and is necessary for proper nervous system function. Preferably, the multi-vitamin and mineral supplement is comprised of about 3 mg of vitamin B1.

Vitamin B2 or riboflavin is necessary for healthy hair, nails, and mucous membranes and is involved in red blood cell formation, antibody production, and overall growth. Preferably, the multi-vitamin and mineral supplement of the present invention is comprised of about 10 mg of vitamin B2.

Vitamin B3 or niacin helps in the production of most of the sex hormones, dilates blood vessels, lowers cholesterol, and helps maintain blood circulation. Niacin is the generic name for a group of compounds which exhibit niacin activity, and includes niacinamide and nicotinic acid. Preferably, in the multi-vitamin and mineral supplement, vitamin B3 is provided as niacinamide. Preferably, the multi-vitamin and mineral supplement is comprised of about 20 mg of vitamin B3. More preferably, the multi-vitamin and mineral supplement is comprised of about 20 mg of vitamin B3 in the form of niacinamide.

Vitamin B6 or pyridoxine is involved in the production of ribonucleic acid (RNA) and deoxyribonucleic acid (DNA) and many other reactions in the body. Pyridoxine refers to and includes three different compounds: pyridoxine, pyridoxamine, and pyridoxal. Preferably, in the multi-vitamin and mineral supplement, vitamin B6 is in the form of pyridoxine hydrochloride. Preferably, the multi-vitamin and mineral supplement is comprised of about 50 mg of vitamin B6. More preferably, the multi-vitamin and mineral supplement is comprised of about 50 mg of vitamin B6 in the form of pyridoxine hydrochloride.

Folic acid is essential in the production of red blood cells, the production of hormones, and the synthesis of DNA. Preferably, the multi-vitamin and mineral supplement is comprised of about 800 mcg of folic acid.

Vitamin B12 or the cobalamins is necessary for overall metabolism, the function of the nervous system, metabolism of folic acid, and the production of red blood cells. There are at least three active forms of cobalamin: cyanocobalamin, hydroxocobalamin, and nitrocobalamin. Preferably, in the multi-vitamin and mineral supplement of the present invention, vitamin B12 is provided in the form of cyanocobalamin. Preferably, the multi-vitamin and mineral supplement is comprised of about 400 mcg of vitamin B12. More preferably, the multi-vitamin and mineral supplement is comprised of about 400 mcg of vitamin B12 in the form of cyanocobalamin.

Biotin is necessary for the metabolism of carbohydrates, proteins, and fats and is needed for healthy skin and hair. Preferably, in the multi-vitamin and mineral supplement, biotin is provided in the form of d-biotin. Preferably, the multi-vitamin and mineral supplement is comprised of about 300 mcg of biotin. More preferably, the multi-vitamin and mineral supplement is comprised of about 300 mcg of biotin in the form of d-biotin.

Pantothenic acid is important for the production of adrenal gland hormones, increases overall energy, and helps convert food into energy. Preferably, in the multi-vitamin and mineral supplement, pantothenic acid is in the form of d-calcium pantothenate. Preferably, the multi-vitamin and mineral supplement is comprised of about 10 mg of pantothenic acid. More preferably, the multi-vitamin and mineral supplement is comprised of about 10 mg of pantothenic acid in the form of d-calcium pantothenate.

Choline is necessary for nervous system function and brain function. It is also important for gall bladder and liver function. Preferably, in the multi-vitamin and mineral supplement, choline is provided in the form choline bitartrate. Preferably, the multi-vitamin and mineral supplement is comprised of about 500 mg of choline. More preferably, the multi-vitamin and mineral supplement is comprised of about 500 mg of choline in the form of choline bitartrate.

Iron is used in the production of hemoglobin and myoglobin. In the multi-vitamin and mineral compound, the iron is dosed in the form of a pharmaceutically acceptable iron compound. As used herein, pharmaceutically acceptable is a component which is suitable for use in humans without undue side effects, such as irritation, toxicity, and allergic response. Useful pharmaceutically acceptable iron compounds include, but are not limited to, ferrous fumarate, ferrous sulfate, carbonyl iron, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes, and combinations thereof. Preferably, the pharmaceutically acceptable iron compound is ferrous fumarate. Preferably, the multi-vitamin and mineral compound is comprised of about 18 mg of iron dosed in a pharmaceutically acceptable iron compound. More preferably, the multi-vitamin and mineral supplement is comprised of about 18 mg of iron dosed in the form of ferrous fumarate.

Iodine helps to metabolize fats, is necessary for proper thyroid function, and reduces fibrocystic breast conditions. In the multi-vitamin and mineral supplement of the present invention, iodine is dosed in the form of a pharmaceutically acceptable iodine compound. Useful pharmaceutically acceptable iodine compounds include, but are not limited to, potassium iodide, sodium iodide, and combinations thereof. Preferably, the pharmaceutically acceptable iodine compound is potassium iodide. Preferably, the multi-vitamin and mineral supplement is comprised of about 150 mcg of iodine dosed in the form of a pharmaceutically acceptable iodine compound. More preferably, the multi-vitamin and mineral supplement is comprised of about 150 mg of iodine dosed in the form of potassium iodide.

Magnesium is used in bone formation and growth, prevents bone loss, relaxes coronary arteries, is used in managing pre-eclampsia, treating cardiac arrhythmias, and managing diabetes. In the multi-vitamin and mineral supplement, magnesium is dosed in the form of a pharmaceutically acceptable magnesium compound. Useful pharmaceutically acceptable magnesium compounds include, but are not limited to, magnesium stearate, magnesium carbonate, magnesium oxide, magnesium hydroxide, magnesium sulfate, and combinations thereof. Preferably, the pharmaceutically acceptable magnesium compound is magnesium oxide. Preferably, the multi-vitamin and mineral supplement is comprised of about 400 mg of magnesium dosed in the form of a pharmaceutically acceptable magnesium compound. More preferably, the multi-vitamin and mineral supplement is comprised of about 400 mg of magnesium dosed in the form of magnesium oxide.

Zinc is required for proper formation of DNA and RNA and is needed for growth and sexual development of women. In the multi-vitamin and mineral supplement of the present invention, zinc is dosed in the form of a pharmaceutically acceptable zinc compound. Pharmaceutically acceptable zinc compounds include, but are not limited to, zinc sulfate, zinc chloride, zinc oxide, and combinations thereof Preferably, the pharmaceutically acceptable zinc compound is zinc oxide. Preferably, the multi-vitamin and mineral supplement is comprised of about 15 mg of zinc dosed in the form of a pharmaceutically acceptable zinc compound. More preferably, the multi-vitamin and mineral supplement is comprised of about 15 mg of zinc dosed in the form of zinc oxide.

Selenium reduces the risk of heart attacks and heart disease, reduces the risk of cancer, protects against metal poisoning, and is synergistic with vitamin E. Preferably, in the multi-vitamin and mineral supplement, selenium is obtained from rice bran chelate. Preferably, the multi-vitamin and mineral supplement is comprised of about 100 mcg of selenium.

Copper helps keep blood vessels elastic, is needed for the formation of elastin and collagen, functions as an iron oxidizer, and is needed for the proper functioning of vitamin C. In the multi-vitamin and mineral supplement, copper is dosed in a pharmaceutically acceptable copper compound. Pharmaceutically acceptable copper compounds include, but are not limited to, cupric oxide, cupric sulfate, cupric gluconate, and combinations thereof. Preferably, the pharmaceutically acceptable copper compound is cupric gluconate. Preferably, the multi-vitamin and mineral supplement is comprised of about 2 mg of copper dosed in the form of a pharmaceutically acceptable copper compound. More preferably, the multi-vitamin and mineral compound is comprised of about 2 mg of copper dosed in the form of cupric gluconate.

Chromium assists in the regulation of glucose metabolism, is used in the synthesis of fatty acids and cholesterol, assists in transporting proteins, lowers LDL blood levels, and raises high density lipoproteins blood levels. In the multi-vitamin and mineral supplement, chromium is dosed in a pharmaceutically acceptable chromium compound. Useful pharmaceutically acceptable chromium compounds include, but are not limited to, yeast-bound chromium, GTF chromium, niacin-bound chromium, and combinations thereof. Preferably, the pharmaceutically acceptable chromium compound is chromium amino acid chelate. Preferably, the multi-vitamin and mineral supplement is comprised of about 65 mcg of chromium dosed in the form of a pharmaceutically acceptable chromium compound. More preferably, the multi-vitamin and mineral supplement is comprised of about 65 mcg of chromium dosed in the form of chromium amino acid chelate.

Potassium is needed to regulate water balance, levels of acidity, blood pressure, and neuromuscular function. Potassium is also required for carbohydrate and protein metabolism. In the multi-vitamin and mineral supplement, potassium is dosed in the form of a pharmaceutically acceptable potassium compound. Useful pharmaceutically acceptable potassium compounds include, but are not limited to, potassium chloride, potassium glycerophosphate, potassium citrate, potassium gluconate, potassium phosphate, and combinations thereof. Preferably, the pharmaceutically acceptable potassium compound is potassium phosphate. Preferably, the multi-vitamin and mineral supplement is comprised of about 400 mg of potassium dosed in the form of a pharmaceutically acceptable potassium compound. More preferably, the multi-vitamin and mineral supplement is comprised of about 400 mg of potassium dosed in the form of potassium phosphate.

Lycopene has been found to reduce the risk of cancer and has antioxidant capabilities. Lycopene is found primarily in tomatoes, red grapefruit, watermelon, and other sources, and is a carotenoid. Preferably, in the multi-vitamin and mineral supplement, the lycopene is obtained from tomatoes. Preferably, the multi-vitamin and mineral supplement is comprised of about 5 mg of lycopene.

Co-enzyme Q10, also known as ubiquinone, is an antioxidant which protects the body from radicals. Co-enzyme Q10 aids metabolic reactions, such as the complex process of transforming food into ATP, and helps people with congestive heart failure and angina. Co-enzyme Q10 is depleted in people taking lovastatin and pravastatin, which are cholesterol lowering drugs. Preferably, the multi-vitamin and mineral supplement is comprised of about 100 mg of Co-enzyme Q10.

The nutritional supplements of the present invention are suitably provided in any suitable dosage form known in the art. For example, the compositions are suitably incorporated into tablets, powders, granules, beads, chewable lozenges, capsules, liquids, or similar conventional dosage forms, using conventional equipment and techniques known in the art. Tablet dosage forms are preferred.

When preparing dosages forms incorporating the compositions of the present invention, the nutritional components are normally blended with conventional excipients such as binders, including gelatin, pregelatinzed starch, and the like; lubricants, such as hydrogenated vegetable oil, stearic acid and the like; diluents, such as lactose, mannose, and sucrose; disintegants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

For preparing the composition from the compounds described by this invention, inert, pharmaceutically acceptable carriers are used which are either solid or liquid form. Solid form preparations include powders, tablets, dispersible granules, capsules, and cachets. A solid carrier is suitably one or more substances which may also act as diluents, flavoring agents, solubilizers, lubricants, suspending agents, binders or tablet disintegrating agents. The solid carrier material also includes encapsulating material. In powders, the carrier is finely divided active compounds. In the tablet, the active compound is mixed with the carrier having the necessary binding properties in suitable proportions and compacted in the shape and size desired. Suitable solid carriers include, but are not limited, to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compounds with encapsulating material as the carrier providing a capsule in which the active component (with or without other carriers) is surrounded by carrier, which is thus in association with it. Tablets, powders, cachets, and capsules may be used in a solid dosage form suitable for oral administration.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations which are intended to be converted, shortly before use, to liquid form preparations for either oral or parental administration. Such liquid forms include solutions, suspensions, and emulsions. These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric contained.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like as well as combinations thereof. The liquid utilized will be chosen with regard to the route of administration.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients.

Determination of the proper dosage for a particular situation is within the skill of the art. For convenience, the total daily dosage may be divided and administered in portions during the day if desired. Controlled and uncontrolled release formulations are also included.

Although the products of the invention are preferably intended for administration to humans, it will be understood that the formulation may also be utilized in veterinary therapy for other animals.

The present invention is further exemplified in the following example It is understood that the example is only for illustrative purposes wherein the claims set forth the scope of the present invention.

EXAMPLE

The effect of the multi-vitamin and mineral supplement of the present invention on blood lipids, serum concentration of vitamins, serum concentration of homocysteine, LDL oxidation rates, plasma glucose levels, and levels of other elements in the blood was studied. One hundred fifty-one human subjects participated in the study.

The participants underwent an initial six week washout period during which no vitamin or mineral supplements, except calcium, were taken. After undergoing a six-week washout period, the participants had blood drawn for blood chemistry analysis. After the washout period, the participants took the prescribed dosage of the multi-vitamin and mineral supplement in the form of three tablets, twice daily with food for six months. Participants returned to have their blood drawn and analyzed at the end of three months of taking the supplement, and again at the end of the six month period. The participants were required to keep a three-day dietary record for the three days immediately prior to each of the blood draws. In addition, the participants were required to fast (to stop eating and drinking everything except water) for twelve hours prior to each blood draw.

All participants completed a vitamin supplement questionnaire as to what supplements were taken before the six week washout period. The questionnaires indicated that 34% were taking a multi-vitamin, 33% were taking vitamin E, 38% were taking vitamin C, 22% were taking beta-carotene, and 13% were taking selenium. At the end of the six months, 2% of the participants were taking vitamin C, 1% were taking vitamin E, and 0.7% were taking a multi-vitamin and beta-carotene supplement.

The demographic and medical information for the participants is shown in Table 1 below.

TABLE 1

| Characteristics of Participants | |
|---|---|
| Female | 48% |
| Age (years) | 50.9 ± 12.3 |
| Non-Hispanic White | 93% |
| Married | 90% |
| Education ≧16 years | 77% |
| Current smokers | 5% |
| Walk or Jog | 61% |
| Weight (kg) | 76.2 ± 17.9 |
| Height (m) | 1.73 ± 0.11 |
| BMI(kg/m$^2$) | 25.3 ± 4.5 |
| History of myocardial infarction | 0.7% |
| History of chest pain with exertion | 2.8% |
| History of stroke | 0.7% |
| History of cancer | 11% |
| History of hypertension | 14% |
| History of high cholesterol | 30% |
| History of diabetes | 0.7% |
| History of thyroid disease | 6% |
| History of arthritis | 17% |
| History of depression | 11% |
| Family history of CVD | 29% |

The blood chemistry analysis of the participants analyzed the level of certain blood lipids, such as cholesterol and triglycerides, and other components present in blood serum. The results of this analysis is shown in Table 2 below.

TABLE 2

| Blood lipids and other measurements in Participants | | | |
|---|---|---|---|
| Variable | Month 0 | Month 3 | Month 6 |
| Cholesterol (mg/dl) | 201.4 ± 41.6 | 199.0 ± 38.3 | 207.6 ± 39.5 |
| HDL-Chol (mg/dl) | 58.6 ± 18.0 | 58.7 ± 17.5 | 59.4 ± 17.9 |
| LDL-Chol (mg/dl) | 122.1 ± 65.0 | 114.8 ± 32.2 | 123.5 ± 33.3 |
| VLDL-Chol (mg/dl) | 24.6 ± 16.1 | 23.9 ± 13.8 | 24.6 ± 14.7 |

TABLE 2-continued

Blood lipids and other measurements in Participants

| Variable | Month 0 | Month 3 | Month 6 |
|---|---|---|---|
| Triglyceride (mg/dl) | 123.3 ± 87.5 | 118.8 ± 73.2 | 121.9 ± 74.4 |
| Glucose (mg/dl) | 98.2 ± 15.8 | 94.1 ± 11.7*** | 94.7 ± 14.4*** |
| Potassium (mEq/L) | 4.5 ± 0.5 | 4.5 ± 0.5 | 4.6 ± 0.4 |
| Sodium (mEq/L) | 139.2 ± 2.0 | 140.2 ± 2.2 | 140.1 ± 2.2 |
| Calcium (mg/dl) | 8.9 ± 0.4 | 9.4 ± 6.1 | 8.9 ± 0.4 |
| Phosphorus (mg/dl) | 3.3 ± 0.4 | 3.3 ± 0.5 | 3.2 ± 0.4 |
| Bilirubin (U/L) | 0.7 ± 0.3 | 0.7 ± 0.3 | 0.7 ± 0.3 |
| ALT (U/L) | 22.5 ± 11.2 | 27.5 ± 19.8*** | 27.4 ± 16.6*** |
| AST (U/L) | 20.2 ± 5.1 | 23.6 ± 8.1*** | 24.0 ± 7.4*** |
| ALP (U/L) | 66.5 ± 15.9 | 64.9 ± 18.4 | 65.4 ± 14.9 |
| All Protein (g/dl) | 7.2 ± 0.4 | 7.3 ± 0.4 | 7.3 ± 0.4 |
| Albumin (g/dl) | 4.5 ± 0.3 | 4.4 ± 0.4 | 4.5 ± 0.4 |
| Uric Acid (mg/dl) | 5.4 ± 1.4 | 5.1 ± 1.3 | 5.1 ± 1.4 |
| Urea Nitrogen (mg/dl) | 15.4 ± 3.8 | 15.2 ± 4.0 | 15.2 ± 3.6 |
| Creatinine (mg/dl) | 1.1 ± 0.2 | 1.1 ± 0.2 | 1.1 ± 0.2 |
| LD (U/L) | 142.1 ± 24.0 | 145.1 ± 32.3 | 139.6 ± 27.1 |
| CK (U/L) | 104.6 ± 68.4 | 111.4 ± 88.6 | 111.4 ± 88.6 |

***$P < 0.0001$ when compared with month 0.

The expected range for total cholesterol is between 130–200 mg/dL. Table 2 shows that the participants had a slightly higher than the expected or normal values for total cholesterol. Cholesterol is further divided into high density cholesterol (HDL), low density cholesterol (LDL), and very low density cholesterol (VLDL) fractions. HDL is known as the good cholesterol because higher levels have been associated with a lower risk of cardiovascular disease and heart attacks. The normal levels for HDL are 45–70 mg/dL for men and 55–85 mg/dL for women. As shown in Table 4, the participants had a normal range of HDL for the duration of the study.

LDL is known as the bad cholesterol as it has been linked to the development of atherosclerosis in the coronary arteries. The normal range for LDL cholesterol is between 65–130 mg/dL. The participants had a normal range of LDL cholesterol, which remained consistent throughout the study, as shown in Table 2.

VLDL is another component of total cholesterol. More research must be conducted on VLDL to better understand its function. The normal range of VLDL is 0–25 mg/dL for men and 0–14 mg/dL for women. The participants had normal VLDL levels from the first visit to the third visit.

ALT, also known as alanine aminotransferase, and AST, also known as aspartate aminotransferase, are enzymes which are related to liver function in general. The normal range for ALT is 0–65 U/L and the normal range for AST is 8–40 U/L. There was a significant increase in these enzymes from the beginning of the study to the sixth month, although these values did not approach or exceed the normal levels as indicated.

Glucose is blood sugar. Significantly high levels of glucose may indicate a diabetic tendency or actual diabetes. Low levels of glucose are suggestive of hypoglycemia. The expected or normal range for glucose is 80–120 mg/dL. Another object of the study was to determine the effect of the supplement on fasting serum glucose. The results are shown in Table 2 and in Table 3 below.

TABLE 3

Effect of Supplement on Fasting Glucose Levels

| Variable | N | Month 0 | Month 3 | Month 6 |
|---|---|---|---|---|
| 80–109 (mg/dl) | 134 | 94.7 ± 6.8 | 91.7 ± 8.0*** | 91.7 ± 13.8*** |
| 110–125 (mg/dl) | 10 | 114.4 ± 3.6 | 110.2 ± 8.7 | 107.8 ± 8.7# |
| 126–205 (mg/dl) | 4 | 173.0 ± 36.0 | 139.0 ± 30.5 | 136.5 ± 27.2 |
| All Subjects | 148 | 98.2 ± 15.8 | 94.1 ± 12.7*** | 94.7 ± 14.3*** |

***$P < 0.0001$ when compared with month 0.
$P < 0.05$ when compared with month 0.

The average of fasting glucose levels significantly decreased from the beginning (98.2 mg/dL), to month 3 (94.1 mg/dL), to the end of the study (94.7 mg/dL). The decrease in plasma glucose levels were presented in 14 subjects with impaired fasting glucose or diabetes (−16.9 mg/dL) and 134 subjects with normal glucose levels (−3.1 mg/dL). These results indicate that the multi-vitamin and mineral supplement may lower plasma glucose levels.

Another objective of the study was to determine if the homocysteine levels lowered after supplementation with the multi-vitamin and mineral supplement of the present invention. As discussed above, homocysteine is not inherently bad, but too much homocysteine may cause problems. High levels of homocysteine confers a risk of vascular disease, increases the risk of atherosclerosis, and may be associated with Alzheimer's disease. The following ranges provide the risk ranges for cardiovascular diseases, as well as other homocysteine-related diseases:

| | |
|---|---|
| 5 micromoles per liter or less - | very low risk |
| 6–9 micromoles per liter | low risk |
| 10–12 micromoles per liter | moderate risk |
| 13–18 micromoles per liter | high risk |
| 19 micromoles per liter or higher | very high risk |

The preferable level of homocysteine is below 10 micromoles per liter.

It has been discovered that folic acid has the potential of dramatically lowering homocysteine levels, particularly when combined with vitamin B6 and B12. Another objective of the study was determine how well vitamin B6, B12, and folic acid were absorbed. The results of the effect of the supplement on serum concentrations of vitamins and homocysteine are shown in Table 4 below.

TABLE 4

Effect of Supplement on The Serum Concentrations of Vitamins and Homocysteine

| Variable | Month 0 | Month 3 | Month 6 |
|---|---|---|---|
| Cysteine (nmol/ml) | 271.7 ± 42.2 | 278.1 ± 41.5 | 281.3 ± 42.5 |
| Homocysteine (nmol/ml) | 7.9 ± 2.4 | 6.7 ± 1.7*** | 6.7 ± 1.9*** |
| Pyridoxal-5-phosphate (pmol/ml) | 75.2 ± 65.1 | 430.0 ± 176.8*** | 391.2 ± 170.3*** |
| Folate (ng/ml) | 9.3 ± 3.4 | 13.1 ± 3.8*** | 12.4 ± 4.0*** |
| Vitamin B 12 (pg/ml) | 454.9 ± 138.2 | 729.3 ± 234.0*** | 800.3 ± 281.4*** |

TABLE 4-continued

Effect of Supplement on The Serum Concentrations of Vitamins and Homocysteine

| Variable | Month 0 | Month 3 | Month 6 |
|---|---|---|---|

***p < 0.0001 when compared with month 0.
**p < 0.0001 when compared with month 0.

As shown in Table 4, the levels of the vitamin B6, B12, and folic acid increased significantly indicating that the vitamins were easily and readily absorbed. As further shown in Table 3, the participants had an average of 7.9 nmol/ml of homocysteine at the first visit and an average of 6.7 nmol/ml of homocysteine at the third visit. At the end of the six month study, the participants had an average 12% reduction in homocysteine levels. As is shown in Table 6 below, those participants with a homocysteine level above 10 nmol/l at the first visit had a 31% reduction in homocysteine levels at the third visit. Therefore, the multi-vitamin and mineral supplement of the present invention may reduce cardiovascular risk by decreasing homocysteine levels.

As discussed above, high levels of LDL cholesterol has been linked to the development of atherosclerosis in the coronary arteries. Clogging of the arteries occurs after LDL cholesterol is oxidized within the blood vessel walls after exposure to free radicals. The white blood cells attempt to remove the damaged LDL cholesterol by engulfing them. After ingesting the LDL cholesterol, the white blood cells cannot rid themselves of the cholesterol and swell, beginning the process of atherosclerosis. LDL cholesterol can fight the free radicals with antioxidants such as vitamin C and E, but before long the antioxidants are depleted and the LDL is left defenseless. Another objective of the study was to determine if vitamin C, E, and beta-carotene in the supplement reduced the oxidation of LDL cholesterol. The results of the effects of the supplement on LDL oxidation kinetics are shown in Tables 5 and 6 below.

TABLE 5

Effect of Supplement on LDL Oxidation Kinetics

| Variable | Month 0 | Month 3 | Month 6 |
|---|---|---|---|
| LDL Oxidation Lag time (minutes) | 57.5 ± 13.9 | 63.5 ± 19.0*** | 63.8 ± 16.3** |
| LDL Oxidation Rate (umol/min/g protein) | 9.7 ± 3.0 | 7.1 ± 2.5*** | 6.0 ± 2.0*** |
| Lipid-Standard? vitamin C | 0.9 ± 0.3 | 1.3 ± 0.4*** | 1.4 ± 0.4*** |
| Lipid-Standard? | 33.0 ± 11.3 | 55.0 ± 23.4*** | 49.5 ± 18.0** |
| vitamin E Lipid-Standard? Beta-Carotene | 0.2 ± 0.2 | 0.4 ± 0.3*** | 0.4 ± 0.3*** |

***p < 0.0001 when compared with month 0.
**P < 0.0001 when compared with month 0.

TABLE 6

Effect of Supplement on the Serum Concentrations of Homocysteine and LDL oxidation

| | Subgroup | | Month 0 | Month 3 | % change (0–3 M) | Month 6 | % change (0–6 M) |
|---|---|---|---|---|---|---|---|
| Homocysteine (nmol/ml) | HCT ≤ 10 (nmol/ml) | 128 | 7.2 ± 1.6 | 6.3 ± 1.3 | −10*** | 6.4 ± 1.7 | −8*** |
| | HCT > 10 (nmol/ml) | 22 | 12.0 ± 2.2 | 8.8 ± 2.0 | −27*** | 8.1 ± 1.9 | −31*** |
| LDL Oxidation Rate (umol/min/g) | LDL ≤ 130 (mg/dl) | 114 | 9.6 ± 3.1 | 7.1 ± 2.7 | −17*** | 5.9 ± 1.9 | −35*** |
| | LDL > 130 (mg/dl) | 28 | 10.2 ± 2.3 | 7.0 ± 2.1 | −22*** | 6.8 ± 2.1 | −24*** |
| Oxidation Lag Time (minutes) | LDL ≤ 130 (mg/dl) | 118 | 57.3 ± 14.2 | 63.2 ± 20.2 | 18*** | 63.7 ± 17.2 | 23*** |
| | LDL > 130 (mg/dl) | 28 | 58.3 ± 12.5 | 64.9 ± 12.5 | 16*** | 63.0 ± 12.8 | 12*** |

***p < 0.0001

Measurement of LDL oxidation include lag time and oxidation rate. Lag time is a measurement (in minutes) of the susceptibility of LDL cholesterol to oxidize, thus, the longer the duration the better. The participants had a significant increases in lag time from an average of 57.5 minutes at the first visit to 63.8 minutes at the third visit. The oxidation rate is the rate at which the LDL oxidizes and a slower rate is preferable. The participants had a significant decrease in oxidation rate from 9.7 umol/min/g protein at the first visit to 6.0 umol/min/g protein at the third visit, a 32% reduction. It is also noted that the blood levels of vitamin C, E, and beta-carotene significantly increased from the first visit to the third visit, thus indicating that these antioxidants were well absorbed. Therefore, the multi-vitamin and mineral supplement of the present invention may reduce cardiovascular risk by decreasing the susceptibility of LDL to oxidation.

While various embodiments of a multi-vitamin and mineral supplement have been disclosed, it should be understood that modifications and adaptations thereof will occur to one skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

Having thus defined the invention, it is claimed:

1. A multi-vitamin and mineral supplement for administration to humans, the supplement comprising:
   about 5000 I.U. of vitamin A;
   about 1000 mg of vitamin C;
   about 400 I.U. of vitamin D;
   about 400 I.U. of vitamin E;
   about 25 mcg of vitamin K;
   about 3 mg of vitamin B1;
   about 10 mg of vitamin B2;
   about 20 mg of vitamin B3;

about 50 mg of vitamin B6;

about 800 mcg of folic acid;

about 400 mcg of vitamin B12;

about 300 mcg of biotin;

about 10 mg of pantothenic acid;

about 18 mg of iron dosed in the form of a pharmaceutically acceptable iron compound;

about 150 mcg of iodine dosed in the form of a pharmaceutically acceptable iodine compound;

about 400 mg of magnesium dosed in the form of a pharmaceutically acceptable magnesium compound;

about 15 mg of zinc dosed in the form of a pharmaceutically acceptable zinc compound;

about 100 mcg of selenium;

about 2 mg of copper dosed in the form of a pharmaceutically acceptable copper compound;

about 65 mcg of chromium dosed in the form of a pharmaceutically acceptable chromium compound;

about 400 mg of potassium dosed in the form of a pharmaceutically acceptable potassium compound;

about 500 mg of choline dosed in the form of a pharmaceutically acceptable choline compound;

about 5 mg of lycopene; and about 100 mg co-enzyme Q-10 dosed in the form of a pharmaceutically acceptable co-enzyme Q-10 compound.

2. The multi-vitamin and mineral supplement of claim 1 wherein the supplement is further comprised of 14 mcg of lutein and zeaxanthine.

3. The multi-vitamin and mineral supplement of claim 1 wherein vitamin A is in the form of natural mixed beta carotene and carotenoids.

4. The multi-vitamin and mineral supplement of claim 1 wherein vitamin E is in the form of d-alpha tocopherol succinate.

5. The multi-vitamin and mineral supplement of claim 1 wherein B3 is in the form of niacinamide.

6. The multi-vitamin and mineral supplement of claim 1 wherein vitamin B6 is in the form of pyridoxine hydrochloride.

7. The multi-vitamin and mineral supplement of claim 1 wherein vitamin B12 is in the form of cyanocobalamin.

8. The multi-vitamin and mineral supplement of claim 1 wherein the biotin is d-biotin.

9. The multi-vitamin and mineral supplement of claim 1 wherein the pantothenic acid is d-calcium pantothenate.

10. The multi-vitamin and mineral supplement of claim 1 wherein the pharmaceutically acceptable iron compound is selected from the group consisting of ferrous fumarate, ferrous sulfate, carbonyl iron, ferrous gluconate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes, and combinations thereof.

11. The multi-vitamin and mineral supplement of claim 10 wherein the pharmaceutically acceptable iron compound is ferrous fumarate.

12. The multi-vitamin and mineral supplement of claim 1 wherein the pharmaceutically acceptable iodine compound is selected from the group consisting of potassium iodide, sodium iodide, and combinations thereof.

13. The multi-vitamin and mineral supplement of claim 12 wherein the pharmaceutically acceptable iodine compound is potassium iodide.

14. The multi-vitamin and mineral supplement of claim 1 wherein the pharmaceutically acceptable magnesium compound is selected from the group consisting of magnesium stearate, magnesium carbonate, magnesium oxide, magnesium hydroxide, magnesium sulfate, and combinations thereof.

15. The multi-vitamin and mineral supplement of claim 14 wherein the pharmaceutically acceptable magnesium compound is magnesium oxide.

16. The multi-vitamin and mineral supplement of claim 1 wherein the pharmaceutically acceptable zinc compound is selected from the group consisting of zinc sulfate, zinc chloride, zinc oxide, and combinations thereof.

17. The multi-vitamin and mineral supplement of claim 16 wherein the pharmaceutically acceptable zinc compound is zinc oxide.

18. The multi-vitamin and mineral supplement of claim 1 wherein the pharmaceutically acceptable copper compound is selected from the group consisting of cupric oxide, cupric sulfate, cupric gluconate, and combinations thereof.

19. The multi-vitamin and mineral supplement of claim 18 wherein the pharmaceutically acceptable copper compound is cupric gluconate.

20. The multi-vitamin and mineral supplement of claim 1 wherein the pharmaceutically acceptable chromium compound is selected from the group consisting of yeast-bound chromium, GTF chromium, niacin-bound chromium, and combinations thereof.

21. The multi-vitamin and mineral supplement of claim 20 wherein the pharmaceutically acceptable chromium compound is chromium amino acid chelate.

22. The multi-vitamin and mineral supplement of claim 1 wherein the pharmaceutically acceptable potassium compound is selected from the group consisting of potassium chloride, potassium glycerophosphate, potassium citrate, potassium gluconate, potassium phosphate, and combinations thereof.

23. The multi-vitamin and mineral supplement of claim 22 wherein the pharmaceutically acceptable potassium compound is potassium phosphate.

24. The multi-vitamin and mineral supplement of claim 1 wherein the choline is choline bitartrate.

25. The multi-vitamin and mineral supplement of claim 1 wherein co-enzyme Q-10 is ubiquinone.

26. The multi-vitamin and mineral supplement of claim 1 wherein the supplement is further comprised of a pharmaceutically acceptable carrier material.

27. The multi-vitamin and mineral supplement of claim 1 which is administered orally once per day.

28. The multi-vitamin and mineral supplement of claim 1 wherein the total daily dosage is divided and administered in portions during the day.

29. The multi-vitamin and mineral supplement of claim 1 wherein the dosage form is enteric coated and compressed into a tablet or filled into hard of soft gelatin capsules.

* * * * *